US011701659B2

(12) United States Patent
Ding et al.

(10) Patent No.: US 11,701,659 B2
(45) Date of Patent: Jul. 18, 2023

(54) MICROFLUIDIC CHIP AND DROPLET SEPARATION METHOD

(71) Applicant: BOE TECHNOLOGY GROUP CO., LTD., Beijing (CN)

(72) Inventors: Ding Ding, Beijing (CN); Lin Deng, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 190 days.

(21) Appl. No.: 17/355,869

(22) Filed: Jun. 23, 2021

(65) Prior Publication Data

US 2022/0168743 A1 Jun. 2, 2022

(30) Foreign Application Priority Data

Nov. 27, 2020 (CN) ........................ 202011363998.3

(51) Int. Cl.

| | |
|---|---|
| ***C12N 15/10*** | (2006.01) |
| ***B01L 3/00*** | (2006.01) |
| ***B01L 7/00*** | (2006.01) |
| ***F28F 3/12*** | (2006.01) |
| ***G01N 35/10*** | (2006.01) |
| ***B29C 45/16*** | (2006.01) |
| ***B29K 25/00*** | (2006.01) |
| ***B29K 105/00*** | (2006.01) |
| ***B29L 31/00*** | (2006.01) |

(52) U.S. Cl.
CPC . *B01L 3/502792* (2013.01); *B01L 2400/0478* (2013.01)

(58) Field of Classification Search
CPC ....... B01L 3/502792; B01L 2400/0478; B01L 2200/0673; B01L 2300/0816; B01L 2300/0864; B01L 2400/02; B01L 2400/0487; B01L 3/502784; B01L 3/5027; B01L 3/502769; B01L 2300/12; B01L 2300/165
See application file for complete search history.

(56) References Cited

U.S. PATENT DOCUMENTS

2003/0124736 A1 * 7/2003 Manz ............... B01L 3/502784 436/180

* cited by examiner

*Primary Examiner* — Jennifer Wecker
*Assistant Examiner* — Oyeleye Alexander Alabi
(74) *Attorney, Agent, or Firm* — Houtteman Law LLC

(57) ABSTRACT

The present disclosure provides a microfluidic chip and a droplet separation method, and belongs to the field of biological chip technology. The microfluidic chip includes a first liquid tank and a second liquid tank opposite to each other and a channel layer therebetween. The channel layer includes a plurality of microfluidic channels separated from each other, first ends of the microfluidic channels are communicated with the first liquid tank, and second ends are communicated with the second liquid tank. The first liquid tank contains sample solution to be detected, and the second liquid tank contains encapsulating liquid. The sample solution to be detected entering the first liquid tank may be separated into a plurality of sample droplets through the microfluidic channels, the separated sample droplets enter the second liquid tank, so that the encapsulating liquid is encapsulated on a surface of each of the plurality of sample droplets.

19 Claims, 6 Drawing Sheets

MICROFLUIDIC CHIP AND DROPLET SEPARATION METHOD

CROSS REFERENCE TO RELATED APPLICATIONS

The present application claims the priority of the Chinese Patent Application No. 202011363998.3 filed on Nov. 27, 2020, the content of which is incorporated herein by reference in its entirety.

TECHNICAL FIELD

The present disclosure relates to the field of biological chip technology, and in particular to a microfluidic chip and a droplet separation method.

BACKGROUND

At present, the microfluidic chip generates droplets mainly in two ways: one is to divide sample solution to be detected into a plurality of droplets through a T-shaped or cross-shaped flow channel structure, then transfer the droplets into a test tube or other microfluidic chips for storage and further operations such as cell labeling, lysis, Polymerase Chain Reaction (PCR) and the like, and then inject the droplets into another microfluidic chip or other equipment for sorting, analysis and other functions, which involves various types of chips and requires lots of manual operations. In this way, the droplets are transferred several times, which has a great influence on the stability the droplets.

The other way is to form a plurality of micropore arrays on a silicon substrate or form a multiway valve made of an elastic polymer material to cause the sample solution to be detected to flow through a plurality of droplet chambers to generate a plurality of droplets. However, in this way, it is very difficult to sort unicells for analysis, it requires liquid to pass in and out many times to form encapsulated droplets, and it is high in chip design and complex in structure.

SUMMARY

The present disclosure provides a microfluidic chip and a droplet separation method.

The embodiment of the present disclosure provides a microfluidic chip, including: a first liquid tank and a second liquid tank opposite to each other and a channel layer between the first liquid tank and the second liquid tank;

the channel layer includes a plurality of microfluidic channels which are separated from each other, first ends of the microfluidic channels are communicated with the first liquid tank, and second ends of the microfluidic channels are communicated with the second liquid tank; the first liquid tank is configured to contain sample solution to be detected, and the second liquid tank is configured to contain encapsulating liquid;

the plurality of microfluidic channels are configured to separate the sample solution to be detected entering the first liquid tank into a plurality of sample droplets, and make the plurality of sample droplets enter the second liquid tank such that each of the plurality of sample droplets is encapsulated by the encapsulating liquid.

In the microfluidic chip provided by the embodiment of the present disclosure, by squeezing the sample solution to be detected entering the first liquid tank into the plurality of microfluidic channels, one sample droplet is separated through each microfluidic channel, the plurality of sample droplets in the plurality of microfluidic channels enter the second liquid tank through the plurality of microfluidic channels, the encapsulating liquid contained in the second liquid tank is encapsulated on a surface of each of the plurality of sample droplets to encapsulate the plurality of sample droplets, such that a desired number of sample droplets are generated quickly and easily by setting the number of the microfluidic channels. Further, the structure of the microfluidic chip provided by the embodiment of the present disclosure is simple and easily realized.

In some embodiments, each of the plurality of microfluidic channels includes a first channel and a second channel which are connected to each other, the first channel is closer to the first liquid tank than the second channel;

the second channel has a proximal end proximal to the first channel, and a distal end distal to the first channel; wherein, an aperture of the distal end is larger than that of the proximal end, and an aperture of the second channel is gradually increased along a direction from the first channel to the second channel, and the aperture of the distal end of the second channel is larger than a diameter of the sample droplet.

In some embodiments, an aperture of the first channel is constant in the direction from the first channel to the second channel, and the aperture of the first channel is smaller than the diameter of the sample droplet.

In some embodiments, an orthographic projection of the first channel on a plane where the first liquid tank is located is within an orthographic projection of the second channel on the plane where the first liquid tank is located.

In some embodiments, an orthographic projection of the first channel on a plane where the first liquid tank is located is circular, and an orthographic projection of the second channel on the plane where the first liquid tank is located is circular.

In some embodiments, the plurality of microfluidic channels extend in a first direction; a plane where the first liquid tank is located is parallel to a plane where the second liquid tank is located; the first direction is perpendicular to an extending direction of the plane where the first liquid tank is located.

In some embodiments, the first liquid tank has a first fluid inlet and a first fluid outlet; the second liquid tank has a second liquid inlet and a second liquid outlet; wherein, an included angle between an extending direction of a first connection line between the first liquid inlet and the first liquid outlet and an extending direction of a second connection line between the second liquid inlet and the second liquid outlet is smaller than 90 degrees.

In some embodiments, the extending direction of the first connection line is parallel to the extending direction of the second connection line.

In some embodiments, the first liquid tank has a first fluid inlet and a first fluid outlet; the second liquid tank has a second liquid inlet and a second liquid outlet;

the microfluidic chip further includes: a first driving device and a second driving device; the first driving device is at the first liquid inlet and is configured to drive the sample solution to be detected to flow; the second driving device is at the second liquid inlet and is configured to drive the encapsulating liquid to flow.

In some embodiments, the first driving device is any one of a pneumatic pump, a plunger pump, and a peristaltic pump; and/or the second driving device is any one of a pneumatic pump, a plunger pump, and a peristaltic pump.

In some embodiments, a lyophobic layer is on an inner wall of each microfluidic channel and is configured to prevent the sample solution to be detected from adhering to the inner wall.

In some embodiments, a material of the lyophobic layer includes a lyophobic group and a reactive group which are connected to each other; the lyophobic group includes an alkane having a carbon number of not less than 6; the reactive group includes at least one of silane, siloxane, oxysilane.

In some embodiments, a material of the channel layer includes at least one of silicon, glass, polymethyl methacrylate, and polycarbonate.

In some embodiments, a bottom surface of the second liquid tank at a side distal to the channel layer is made of a transparent material.

The present disclosure also provides a droplet separation method using a microfluidic chip, wherein the microfluidic chip includes: a first liquid tank and a second liquid tank opposite to each other and a channel layer between the first liquid tank and the second liquid tank; the channel layer includes a plurality of microfluidic channels which are separated from each other, first ends of the microfluidic channels are communicated with the first liquid tank, and second ends of the microfluidic channels are communicated with the second liquid tank; the first liquid tank contains sample solution to be detected, and the second liquid tank contains encapsulating liquid; the droplet separation method includes the steps of enabling the sample solution to be detected entering the first liquid tank to be separated into a plurality of sample droplets through the plurality of microfluidic channels with the plurality of separated sample droplets entering the second liquid tank, and causing the encapsulating liquid to be encapsulated on a surface of each of the plurality of sample droplets.

In some embodiments, a density of the sample solution to be detected is greater than that of the encapsulating liquid, and the droplet separation method includes steps of: causing the first liquid tank to be below the second liquid tank; opening a second liquid inlet and a second liquid outlet, such that the encapsulating liquid flows into the second liquid tank; and opening a first liquid inlet, closing a first liquid outlet, such that the sample solution to be detected enters the first liquid tank, and pressure in the first liquid tank is gradually increased, so that under the pressure, the sample solution to be detected flows upward from the first ends of the first channels of the plurality of microfluidic channels, enters the plurality of first channels, and is squeezed by the first channels to be separated into a plurality of sample droplets, and the plurality of separated sample droplets enter the second liquid tank, gradually recover from deformation, and finally, enter the upper second liquid tank from the distal ends of the second channels, and the encapsulating liquid is encapsulated on the surface of each of the plurality of sample droplets to form an encapsulating layer.

In some embodiments, after forming the encapsulating layer, the droplet separation method further includes: closing the second liquid outlet, opening the first liquid outlet, such that the pressure of the second liquid tank is increased, the sample droplets are pressed downward, the sample droplets sink and move toward the lower second channels, such that the sample droplets are stopped at the proximal ends of the second channels.

In some embodiments, a density of the sample solution to be detected is lower than that of the encapsulating liquid, and the droplet separation method includes steps of: causing the first liquid tank to be above the second liquid tank; opening a second liquid inlet and a second liquid outlet, such that the encapsulating liquid flows into the second liquid tank; and opening a first liquid inlet, closing a first liquid outlet, such that the sample solution to be detected enters the first liquid tank, and pressure in the first liquid tank is gradually increased, so that the sample solution to be detected flows downward from the first ends of the first channels of the plurality of microfluidic channels, enters the plurality of first channels, and is squeezed by the first channels to separate a plurality of sample droplets, and the plurality of separated sample droplets enter the second liquid tank, gradually recover from deformation, and finally, enter the lower second liquid tank from the distal ends of the second channels, and the encapsulating liquid is encapsulated on the surface of each of the plurality of sample droplets to form an encapsulating layer.

In some embodiments, after forming the encapsulating layer, the droplet separation method further includes: closing the second liquid outlet, opening the first liquid outlet, such that the pressure of the second liquid tank is increased, the sample droplets are pressed upwards, the sample droplets float and move toward the upper second channels, such that the sample droplets are stopped at the proximal ends of the second channels.

DETAIL DESCRIPTION OF EMBODIMENTS

Figure 1:
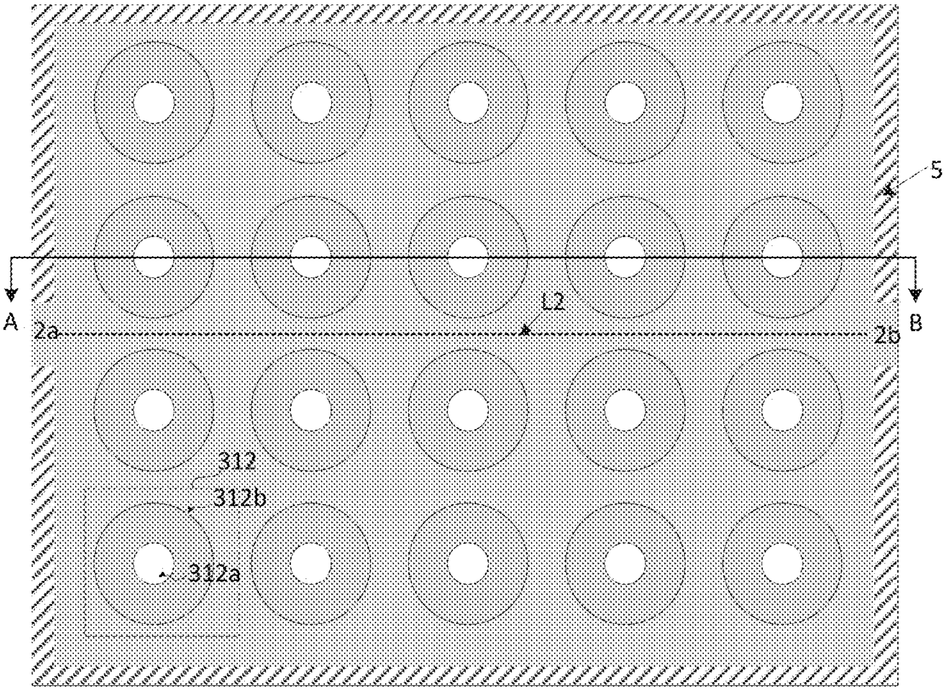
FIG. 1 is a top view (second channel side) of a microfluidic chip according to an embodiment of the present disclosure.

To make objects, technical solutions and advantages of the present disclosure more clear, the present disclosure will be described in further detail with reference to the drawings. It is apparent that the described embodiments are only some embodiments of the present disclosure, not all embodiments. All other embodiments, which may be derived by a person skilled in the art from the embodiments disclosed herein without making any creative effort, shall fall within the protection scope of the present disclosure.

The shapes and sizes of the components shown in the drawings are not necessarily drawn to scale, but are merely for the purpose of facilitating easy understanding of the contents of the present embodiments of the present disclosure.

Unless defined otherwise, technical or scientific terms used herein should have the same meaning as commonly understood by one of ordinary skill in the art to which the present disclosure belongs. The terms of "first" "second", and the like used in the present disclosure are not intended to indicate any order, quantity, or importance, but rather are used for distinguishing one element from another. Further, the term "a", "an", "the", or the like does not denote a limitation of quantity, but rather denotes the presence of at least one element. The term "comprising", "including", or the like, means that the element or item preceding the term contains the element or item listed after the term and the equivalent thereof, but does not exclude the presence of any other element or item. The term "connected", "coupled", or the like is not limited to physical or mechanical connections, but may include electrical connections, whether direct or indirect connections. The terms "upper", "lower", "left", "right", and the like are used only for indicating relative positional relationships, and when the absolute position of the object being described is changed, the relative positional relationships may also be changed accordingly.

The embodiment of the present disclosure is not limited to the embodiments shown in the drawings, but includes modifications of configurations formed based on a manufacturing process. Thus, regions illustrated in the drawings have schematic properties, and shapes of the regions shown in the drawings illustrate specific shapes of regions of elements, but are not intended to be limiting.

Figure 2:
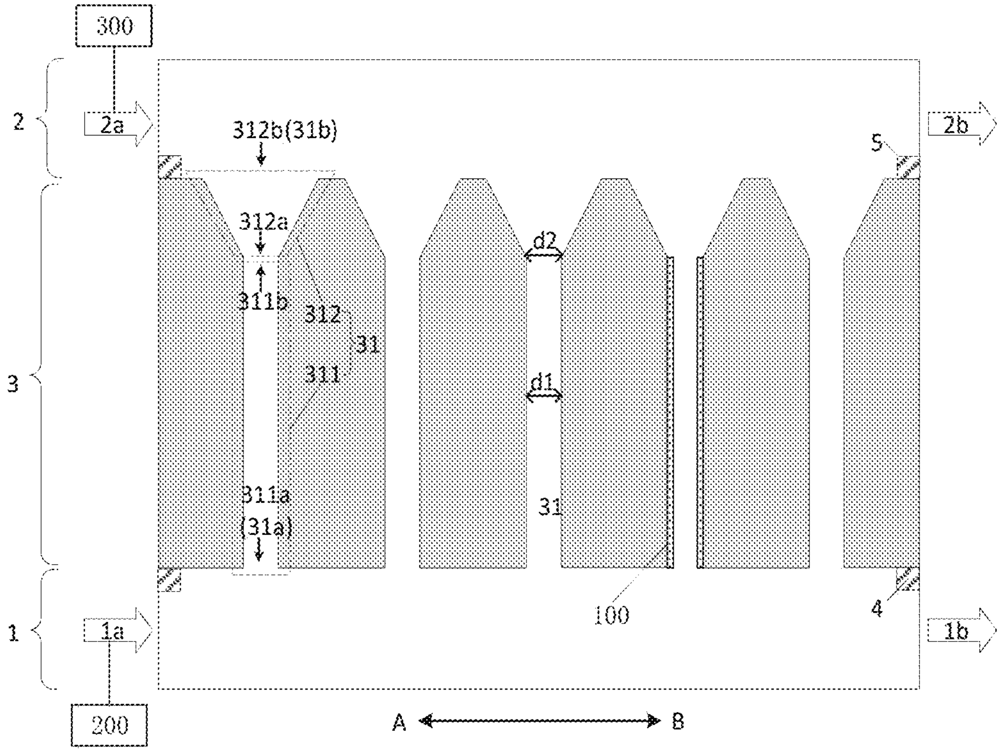
FIG. 2 is a sectional view of the microfluidic chip taken along a direction A-B of FIG. 1.

As shown in FIGS. 1 and 2, an embodiment of the present disclosure provides a microfluidic chip. FIG. 1 is a top view of the microfluidic chip provided in this embodiment, and FIG. 2 is a cross-sectional view of the microfluidic chip taken along a direction A-B in FIG. 1. The microfluidic chip may include a first liquid tank 1 and a second liquid tank 2 opposite to each other, and a channel layer 3 connected between the first liquid tank 1 and the second liquid tank 2. The channel layer 3 includes a plurality of microfluidic channels 31 which are separated from each other, first ends 31*a* of the plurality of microfluidic channels 31 are communicated with the first liquid tank 1, and second ends 31*b* of the plurality of microfluidic channels 31 are communicated with the second liquid tank 2. The first liquid tank 1 contains a sample solution to be detected, which may include an aqueous phase solution and biomolecules, a reaction reagent and the like which are mixed in the aqueous phase solution; the second liquid tank 2 contains encapsulating liquid, which may include an oil phase solution and a stabilizer mixed in the oil phase solution, and the like.

Specifically, when the microfluidic chip generates droplets, firstly, the sample solution to be detected enters the first liquid tank 1, and the sample solution to be detected is driven to enter the plurality of microfluidic channels 31 from the first ends 31*a* of the microfluidic channels 31, and one sample droplet 01 is separated from each microfluidic channel 31. Thus, a plurality of sample droplets 01 are separated from the plurality of microfluidic channels 31 after the sample solution to be detected enters the plurality of microfluidic channels 31; then, the plurality of sample droplets 01 enter the second liquid tank 2 from the second ends 31*b* of the microfluidic channels 31, and flow into the encapsulating liquid in the second liquid tank 2. Because the sample solution to be detected forming the sample droplets 01 is the aqueous solution, and the encapsulating liquid is an oily solution, which are not dissolved, the encapsulating liquid will wrap a surface of each sample droplet 01 in the plurality of sample droplets 01 to form an encapsulating layer 02, the sample droplet 01 is encapsulated in the encapsulating layer 02, and the stabilizer in the encapsulating liquid will increase the stability of the encapsulating layer 02, and finally the sample droplets 01 with a stable encapsulation environment are formed. By setting the number of microfluidic channels 31 in the channel layer 3, a desired number of sample droplets 01 may be formed, such that a large number of sample droplets 01 may be generated quickly and conveniently; and the generation of the sample droplets 01 may be realized only through the first liquid tank 1, the second liquid tank 2 and the channel layer 3, and the structure is simple and easy to be obtained. By adjusting parameters such as a flow rate of the sample solution to be detected in the first liquid tank 1 and a proportion of biomolecules, reaction reagents and aqueous phase solution in the sample solution to be detected, the number of the biomolecules and the reaction reagents in each sample droplet 01 may be controlled, so that the requirements of various sample droplets 01 may be met. For example, the sorting of unicells, the sorting of multiple cells and the like may be performed. The sample droplet 01 is encapsulated by the encapsulating layer 02, so that one sample droplet 01 may be regarded as a micro-reactor, biomolecules and reaction reagents in the sample droplet 01 may directly react in the encapsulating layer 02 without being transferred into any other equipment, reducing the probability of breakage, deformation and the like of the sample droplets 01.

It should be noted that the microfluidic chip provided in the embodiment of the present disclosure may perform various types of biological detection, sort various types of biomolecules, and the biomolecules and the reaction reagents of the sample solution to be detected change according to different types of biological detection. For example, if the microfluidic chip performs nucleic acid extraction, the biomolecules of the sample solution to be detected are nucleic acid (e.g., ribonucleic acid, deoxyribonucleic acid, nucleotide, etc.), the reaction reagents may be various lysis reagents, such as lysis reagents including Tris (hydroxymethyl) aminomethane hydrochloride (Tris-HCl), sodium chloride (NaCl), ethylphenyl polyethylene glycol (NP-40), sodium dodecyl sulfate (SDS), etc., and each sample droplet 01 may have at least one nucleic acid molecule and lysis reagent. For another example, if the microfluidic chip performs membrane protein labeling, the biomolecules may be hemoglobin, the reaction reagents may be dye reagent, such as fluorescein Isothiocyanate (FITC), etc., and each sample droplet 01 may have at least one hemoglobin and dye reagent. The microfluidic chip provided by the embodiment of the present disclosure may be adapted to various biological detections, and is not limited herein.

Figure 3:
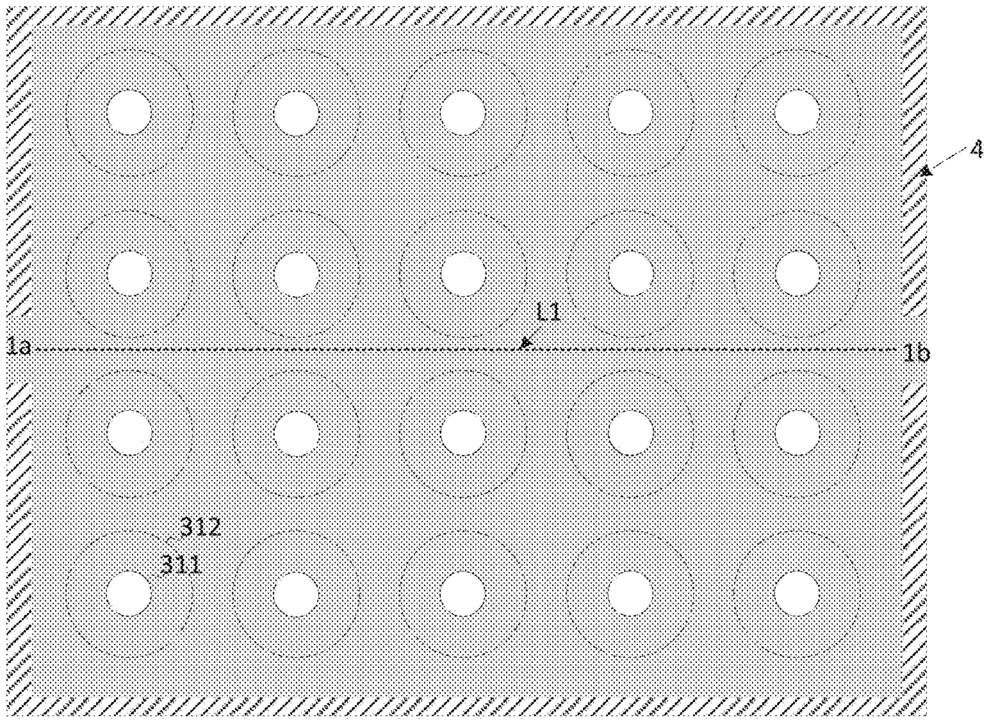
FIG. 3 is a top view (first channel side) of a microfluidic chip according to an embodiment of the present disclosure.

In some examples, as shown in FIGS. 1 to 3, FIG. 3 is a top view of the microfluidic chip viewed from a direction from the first liquid tank 1 to the second liquid tank 2. The channel layer 3 includes the plurality of microfluidic channels 31 separated from each other, that is, the channel layer 3 has a plurality of cavities separated from each other, each cavity defining one microfluidic channel 31. Each microfluidic channel 31 may include a first channel 311 and a second channel 312 connected to each other, wherein the first channel 311 is closer to the first liquid tank 1 than the second channel 312. The first channel 311 has a first end 311*a* close to the first liquid tank 1 and a second end 311*b* distal to the first liquid tank 1; the second channel 312 has a proximal end 312*a* close to the first channel 311 and a distal end 312*b* distal to the first channel 311, the second end 311*b* of the first channel 311 is connected to the proximal end 312*a* of the second channel 312, so that the first channel 311 and the second channel 312 form an integral microfluidic channel 31. It should be understood that in this case, the first end 311*a* of the first channel 311 serves as the first end 31*a* of the microfluidic channel 31, and the distal end 312*b* of the second channel 312 serves as the second end 31*b* of the microfluidic channel 31.

Further, referring to FIGS. 1 and 2, specific shapes of the first channel 311 and the second channel 312 may be various shapes. For example, an aperture of the distal end 312*b* of the second channel 312 is larger than that of the proximal end 312*a*, and an aperture of the second channel 312 relatively distal to the first channel 311 is not smaller than that relatively close to the first channel 311. That is, in the direction of the first channel 311 toward the second channel 312, the aperture of the second channel 312 gradually increases to form a funnel-shaped second channel 312, and the aperture d2 of the proximal end 312*a* of the second channel 312 is larger than a diameter d3 of the sample droplet 01, since the aperture of the distal end 312*b* of the second channel 312 is larger than the aperture d2 of the proximal end 312*a*, the aperture of the distal end 312*b* is larger than the diameter d3 of the sample droplet 01, so that after the plurality of sample droplets 01 enter the second liquid tank 2 and the encapsulating liquid forms the encapsulating layer 02 on the surface of each sample droplet 01, the feeding of the liquid into the first liquid tank 1 may be stopped, to reduce a pressure in the first liquid tank 1, so that the plurality of sample droplets 01 are moved from the second liquid tank 2 toward the first liquid tank 1, gradually approach the distal end 312*b* of the second channel 312, and descend to the proximal end 312*a* of the second channel 312, and because the aperture d2 of the proximal end 312*a* is smaller than the diameter d3 of the sample droplet 01, the sample droplets 01 will stay at the proximal end 312*a* of the second channel 312, and cannot move in the direction approaching the first liquid tank 1, that is, cannot enter the first channel 311, and may be limited by the second channel 312 at the proximal end 312*a*, so that the funnel-shaped second channel 312 may position the sample droplets 01, and after the sample droplets 01 are positioned, the sample droplets 01 may be directly observed in a direction of an outer surface at a side of the second liquid tank 2 distal to the channel layer 3, without transferring the sample droplets 01 to other observation equipment for observation, thereby reducing the probability of breakage, deformation and the like of the sample droplets 01 during the transfer process.

Further, referring to FIGS. 1 and 3, the aperture of the first channel 311 may be constant at each position. That is, the aperture d1 of the first channel 311 has the same (or almost the same) value in a length direction of the first channel 311, and the aperture d1 of the first channel 311 is smaller than the diameter d3 of the sample droplet 01, so that during the process that the sample solution to be detected flows from the first liquid tank 1 into the microfluidic channel 31, that is, into the first channel 311, the sample solution to be detected is squeezed in the first channel 311 until the sample solution is broken into an independent sample droplet 01, and then the sample droplet 01 in the squeezed state flows from the second end 311*b* of the first channel 311 into the second channel 312, and gradually recovers from the squeezed state to the nearly circular sample droplet 01 during the process that the sample droplet 01 in the squeezed state flows from the proximal end 312*a* to the distal end 312*b* of the second channel 312.

In some examples, a length of the microfluidic channel 31 formed by connecting the first channel 311 and the second channel 312 may be set arbitrarily. For example, the length of the microfluidic channel 31 may be between 100 and 1000 micrometers, which is not limited herein.

In some examples, referring to FIG. 3, each dashed circle in FIG. 3 is a position of an orthographic projection of the second channel 312 on a plane where the first liquid tank 1 is located. The first channel 311 and the second channel 312 may extend in different directions or in the same direction. If the first channel 311 and the second channel 312 extend in the same direction, an orthographic projection of the first channel 311 on the plane where the first liquid tank 1 is located in an orthographic projection of the second channel 312 on the plane where the first liquid tank 1 is located. Further, the first channel 311 may be disposed opposite to the second channel 312, that is, a central axis of the first channel 311 in the length direction may coincide with a central axis of the second channel 312 in the length direction.

In some examples, the plurality of microfluidic channels 31 may extend in any direction, for example, in a direction parallel to the plane where the first liquid tank 1 is located, or in a direction oblique to the plane where the first liquid tank 1 is located, and the first channel 311 and the second channel 312 of the microfluidic channel 31 may extend in different directions. For example, referring to FIG. 2, the plane where the first liquid tank 1 is located is parallel (or approximately parallel) to the plane where the second liquid tank 2 is located, that is, a fluid surface of the first liquid tank 1 is parallel (or approximately parallel) to that of the second liquid tank 2. The plurality of microfluidic channels 31 in the channel layer 3 extend in a first direction, which is perpendicular (or approximately perpendicular) to an extending direction of the plane where the first liquid tank 1 (or the second liquid tank 2) is located, that is, the microfluidic channels 31 are vertical channels. The sample solution to be detected in the first liquid tank 1 is divided into a plurality of sample droplets 01 flowing into the second liquid tank in the vertical direction, that is, a flow surface of the sample solution to be detected in the first liquid tank 1 is parallel (or approximately parallel) to that of the encapsulating liquid in the second liquid tank 2, and the sample solution to be detected is divided into a plurality of sample droplets 01 flowing into the second liquid tank 2 along the plurality of microfluidic channels 31, and the flow direction of the sample droplets is perpendicular (or approximately perpendicular) to the flow surface of the sample solution to be detected, and is also perpendicular (or approximately perpendicular) to the flow surface of the encapsulating liquid. Alternatively, the extending direction of the microfluidic channel 31 may be other directions, and is not limited herein.

In some examples, the shapes of the first channel 311 and the second channel 312 may include various shapes. For example, the first channel 311 and/or the second channel 312 may be a circular channel, a rectangular channel, an oval channel, or an irregularly-shaped channel, and the like, which is not limited herein. Taking the first channel 311 and/or the second channel 312 as the circular channel as an example, an orthographic projection of the first channel 311 on the plane where the first liquid tank 1 is located is circular, and an orthographic projection of the second channel 312 on the plane where the first liquid tank 1 is located is circular. It should be noted that the channel shape defining the first channel 311 and/or the second channel 312 may be defined by a shape of a cross section of the first channel 311 and/or the second channel 312 taken along a direction perpendicular to the length direction. For example, the second channel 312 may be a circular funnel-shaped channel, and the aperture of the second channel 312 gradually increases in a direction from the proximal end 312*a* to the distal end 312*b* of the second channel 312, but a cross section of the second channel 312 taken along any position perpendicular to the length direction of the second channel 312 is circular, so that the second channel 312 is called a circular channel.

In some examples, referring to FIGS. 1 to 3, the first liquid tank 1 may be an accommodation space defined by a hollow housing, the hollow housing forming the first liquid tank 1 is fixed to the channel layer 3 by a first adhesive layer 4, the first adhesive layer 4 is located in a peripheral region of a surface on a side of the channel layer 3 proximal to the first liquid tank 1, and is located between the channel layer 3 and the first liquid tank 1; similarly, the second liquid tank 2 may be an accommodation space defined by a hollow housing, the hollow housing forming the second liquid tank 2 is fixed to the channel layer 3 through a second adhesive layer 5, and the second adhesive layer 4 is located in a peripheral region of a surface on a side of the channel layer 3 proximal to the second liquid tank 2 and located between the channel layer 3 and the second liquid tank 2. The first adhesive layer 1 and the second adhesive layer 2 may be various materials having adhesive property, such as double-sided adhesive, optical adhesive, etc., which is not limited here.

In some examples, with continued reference to FIGS. 1 to 3, the first liquid tank 1 has a first liquid inlet 1*a* and a first liquid outlet 1*b*, and the sample solution to be detected flows in the first liquid tank 1 from the first liquid inlet 1*a* and then flows out from the first liquid outlet 1*b*. The second liquid tank 2 has a second liquid inlet 2*a* and a second liquid outlet 2*b*, and the encapsulating liquid flows the second liquid tank 2 in from the second liquid inlet 2*a* and then flows out from the second liquid outlet 2*b*. When the droplets are generated, the sample solution to be detected and the encapsulating liquid may be kept in a flowing state, and a flow direction of the sample solution to be detected may be controlled by controlling the flow rate of the sample solution to be detected and the flow rate of the encapsulating liquid. Specifically, the flow rate of the sample solution to be detected may be smaller than the flow rate of the encapsulating liquid, and a pressure generated by the sample solution to be detected in the first liquid tank 1 is relatively large, so as to provide a driving force to enable the sample solution to be detected to flow into the plurality of microfluidic channels 31 and then flow into the second liquid tank 2. Referring to FIG. 3, in order to make the pressure difference generated by the flow of the sample solution to be detected in the first liquid tank 1 and the flow of the encapsulating liquid in the second liquid tank 2 sufficient, an included angle between an extending direction of a first connection line L1 between the first liquid inlet 1*a* and the first liquid outlet 1*b* of the first liquid tank 1 and an extending direction of a second connection line L2 between the second liquid inlet 2*a* and the second liquid outlet 2*b* of the second liquid tank 2 is smaller than 90°, that is, the first connection line L1 is not perpendicular to the second connection line L2, so that the flow direction of the sample solution to be detected flowing from the first liquid inlet 1*a* to the first liquid outlet 1*b* and the flow direction of the encapsulating liquid flowing from the second liquid inlet 2*a* to the second liquid outlet 2*b* are not perpendicular to each other. Further, the sample solution to be detected may be ensured to flow into the microfluidic channels 31 more easily. In some examples, the extending direction of the first connection line L1 and the extending direction of the second connection line L2 may be parallel to each other, that is, the included angle between the first connection line L1 and the second connection line L2 is 0°, so that the sample solution to be detected may flow into the microfluidic channels 31 more easily.

In some examples, the sample solution to be detected in the first liquid tank 1 may be driven to flow into the second liquid tank 2 through the plurality of microfluidic channels 31 in various ways. For example, the microfluidic chip may further include a first driving device 200 and a second driving device 300. The first driving device 200 is disposed at the first liquid inlet 1*a*, the first driving device 200 drives the sample solution to be detected to flow from the first liquid inlet 1*a* to the first liquid outlet 1*b*, and the flow rate of the sample solution to be detected may be controlled by adjusting a power of the first driving device 200; the second driving device 300 is disposed at the second liquid inlet 2*a*, the second driving device 300 drives the encapsulating liquid to flow from the second liquid inlet 2*a* to the second liquid outlet 2*b*, and the flow rate of the encapsulating liquid may be controlled by adjusting a power of the second driving device 300. By controlling the power of the first driving device 200 and the second driving device 300, the flow rate of the sample solution to be detected may be smaller than that of the encapsulating liquid, and the pressure generated by the sample solution to be detected in the first liquid tank 1 is relatively large, so as to provide a driving force to enable the sample solution to be detected to flow into the plurality of microfluidic channels 31 and then flow into the second liquid tank 2, thereby forming the plurality of sample droplets 01 each having the encapsulating layer 02.

In some examples, the first driving device 200 and the second driving device 300 may include various types of driving devices. For example, the first driving device 200 may be any one of a pneumatic pump, a plunger pump, and a peristaltic pump, and the second driving device 300 may also be any one of a pneumatic pump, a plunger pump, and a peristaltic pump, which is not limited here.

There may be two placement modes for placing the microfluidic chip provided by the embodiment of the present disclosure, which correspond to different density ratios of the sample solution to be detected and the encapsulating liquid, respectively. Specifically, the first and second modes will be described as examples.

First Mode

Figure 4:
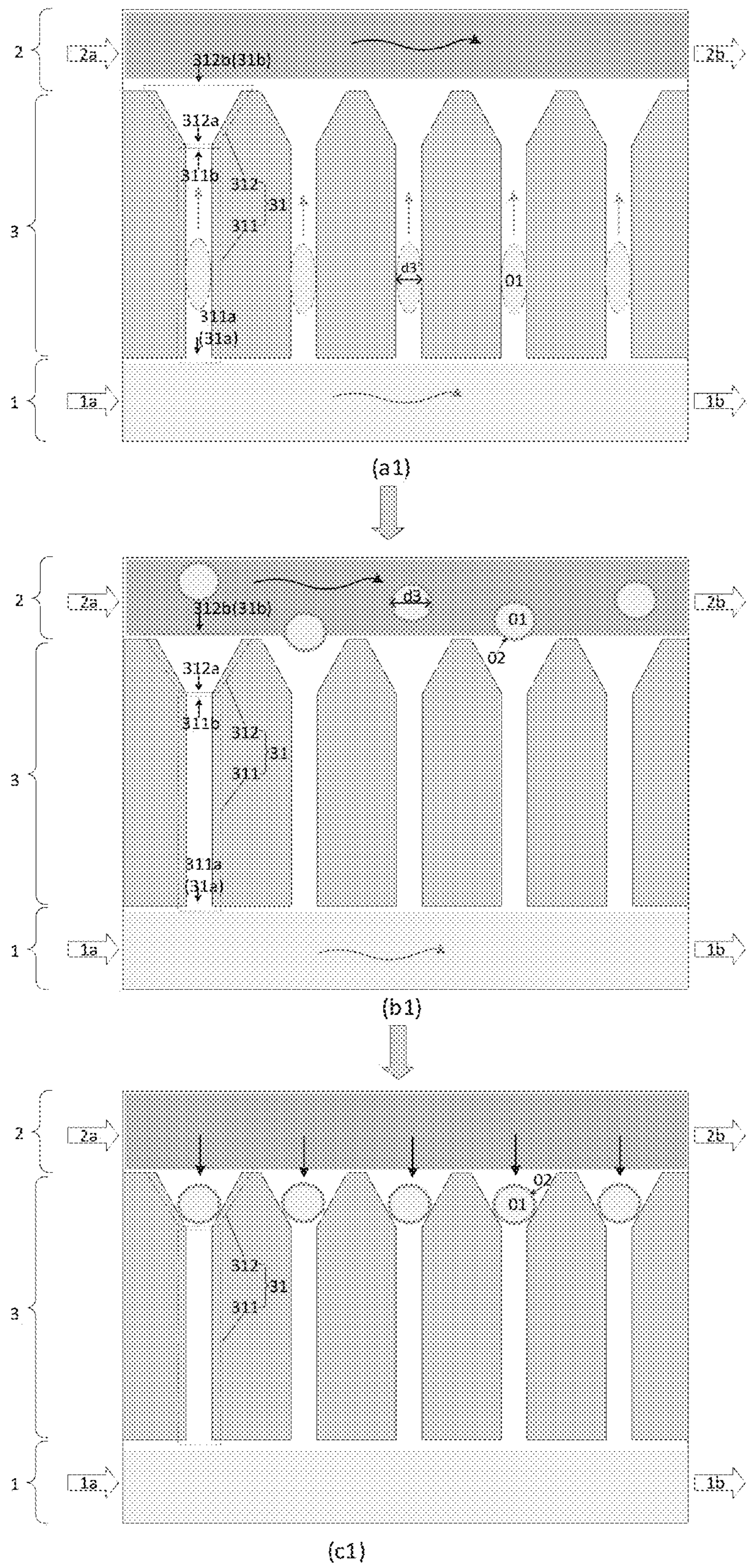
FIG. 4 is a schematic diagram illustrating a procedure of generating sample droplets by a microfluidic chip (upright) according to an embodiment of the present disclosure.

Referring to FIG. 4, if the density of the liquid to be detected is greater than that of the encapsulating liquid, the microfluidic chip may be used in an upright mode, that is, the first liquid tank 1 is disposed close to a table top on which the microfluidic chip is disposed, and the second liquid tank 2 is disposed distal to the table top on which the microfluidic chip is disposed. That is, as shown in FIG. 4, the first liquid tank 1 is disposed below the second liquid tank 2. The generated droplets may be observed from the direction of the second liquid tank 2.

Figure 6:
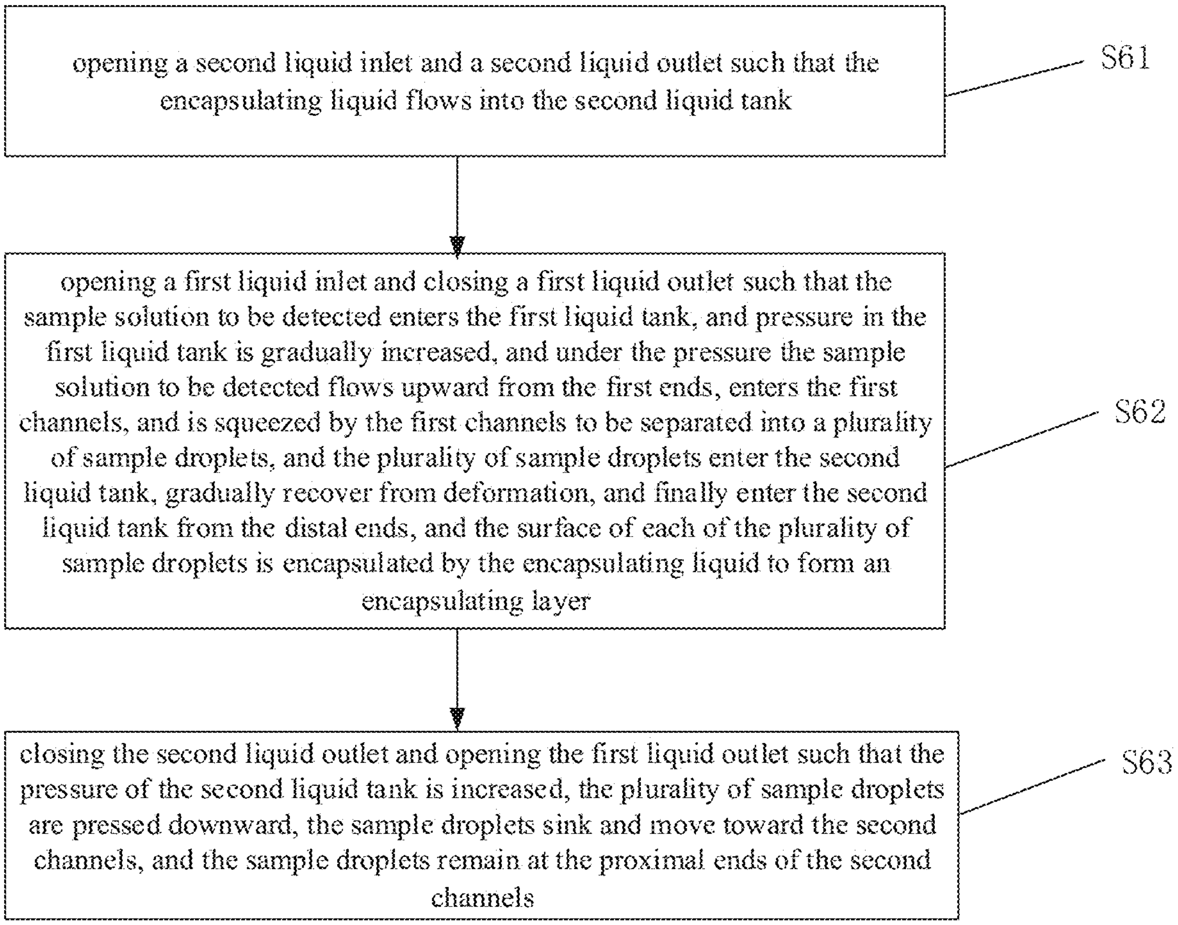
FIG. 6 is a flowchart of a droplet separation method performed by a microfluidic chip according to an embodiment of the present disclosure.

In the embodiment of generating droplets in the upright mode, as shown in FIG. 6, firstly, in step S61, referring to FIG. 4(*a*1), the first liquid inlet 1*a* is opened, the first liquid outlet 1*b* is closed, the sample solution to be detected enters the first liquid tank 1; the second liquid inlet 2*a* is opened, the second liquid outlet 2*b* is opened, the encapsulating liquid flows into the second liquid tank 2; the pressure of the first liquid tank 1 gradually increases, so that the sample solution to be detected flows upward from the first end 311*a* of the first channels 311 of the microfluidic channels 31, enters the first channels 311, and is squeezed by the first channels 311, thereby extracting a plurality of sample droplets 01. The increase of the flow rate of the liquid to be detected may accelerate the increase of the pressure of the first liquid tank 1, so that droplets may be generated more quickly. Alternatively, the first liquid outlet 1*b* and the second liquid outlet 2*a* may both be kept open, such that the flow rate of the liquid to be detected is greater than the flow rate of the encapsulating liquid, and the pressure of the first liquid tank 1 is gradually increased.

Further, in step S62, referring to FIGS. 4(*a*1)-(*b*1), the plurality of sample droplets 01 enter the second channels 312 from the second ends 311*b* of the first channels 311, gradually recover from deformation, and finally enter the upper second liquid tank 2 from the distal ends 312*b* of the second channels 312, and flow into the encapsulating liquid in the second liquid tank 2. Since the sample solution to be detected forming the sample droplets 01 is the aqueous phase solution and the encapsulating liquid is the oily solution, the encapsulating liquid will wrap the surface of each sample droplet 01 of the plurality of sample droplets 01 to form the encapsulating layer 02, so as to encapsulate the sample droplet 01 in the encapsulating layer 02, and the stabilizer in the encapsulating liquid will increase the stability of the encapsulating layer 02, and finally, the sample droplets 01 with stable encapsulation environment are formed.

Further, in step S63, referring to FIGS. 4(*b*1)-(*c*1), the second liquid outlet 2*b* is closed, the first liquid outlet 1*b* is opened, such that the pressure of the second liquid tank 2 is increased, the sample droplets 01 are pressed downward. Since the density of the sample solution to be detected forming the sample droplets 01 is greater than that of the encapsulating liquid, the sample droplets 01 sink and move toward the lower second channels 312. Since the diameter d2 of the proximal end 312*a* of the second channel 312 is smaller than the diameter d3 of the sample droplet 01, the sample droplets 01 are finally stopped at the proximal ends 312*a* of the second channels 312. Since the density of the sample solution to be detected is greater than that of the encapsulating liquid, the sample droplets 01 naturally stay at the proximal ends 312*a* of the second channels 312, so that the sample droplets 01 are positioned, and the generation process of the sample droplets 01 is completed. In this embodiment, after the sample droplets 01 are generated and positioned, the sample droplets 01 at the proximal ends 312*a* of the respective second channels 312 may be observed from above the microfluidic chip, i.e., from the outside of a side of the second liquid tank 2 distal to the channel layer 3, so that the sample droplets 01 are not transferred.

Second Mode

Figure 5:
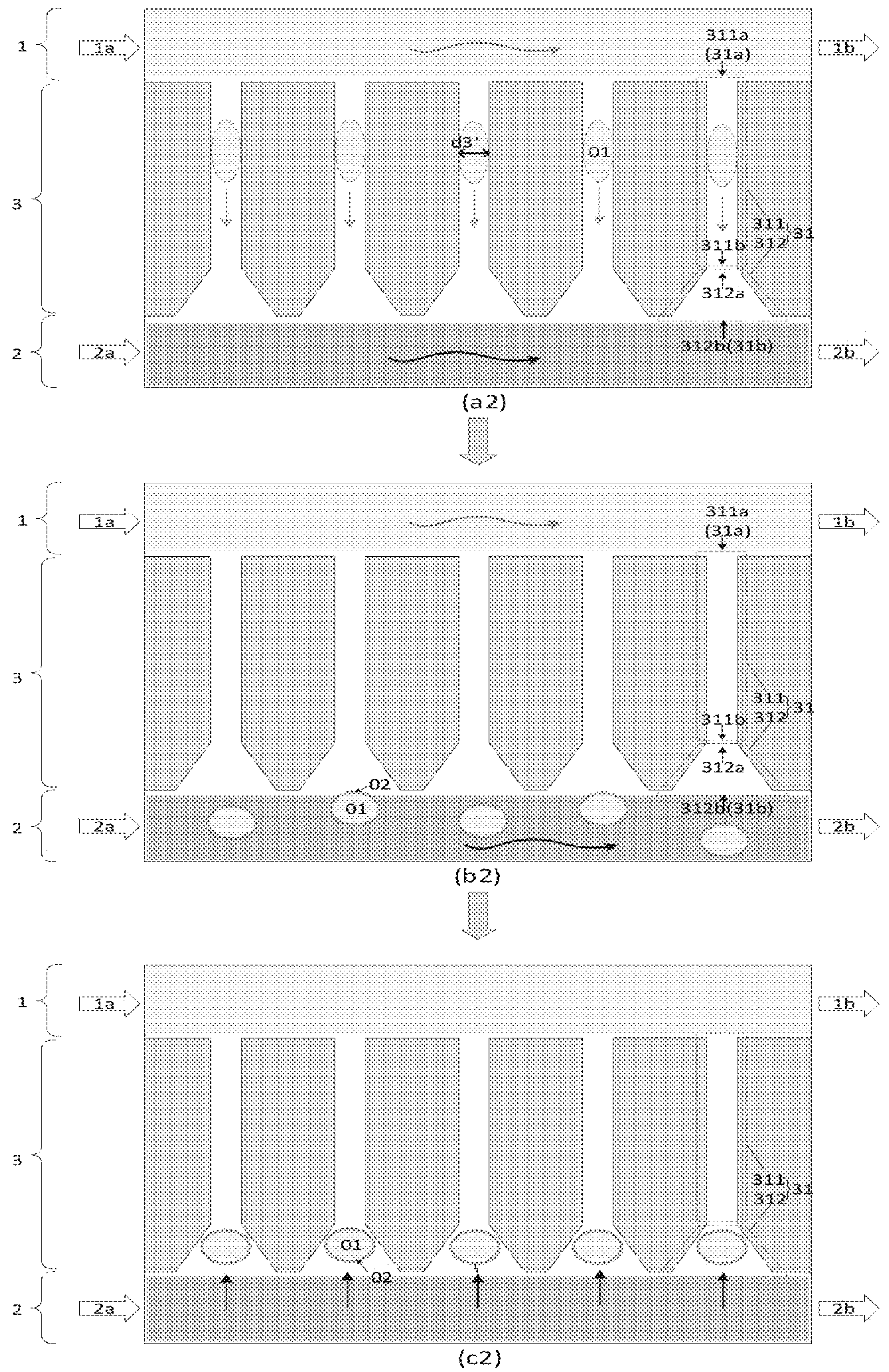
FIG. 5 is a schematic diagram illustrating a procedure of generating sample droplets by a microfluidic chip (inverted) according to an embodiment of the present disclosure.

Referring to FIG. 5, if the density of the liquid to be detected is less than that of the encapsulating liquid, the microfluidic chip may be used in an inverted mode, that is, the second liquid tank 2 is disposed close to the table top on which the microfluidic chip is disposed, and the first liquid tank 1 is disposed distal to the table top on which the microfluidic chip is disposed. As seen in FIG. 5, that is, the first liquid tank 1 is disposed above the second liquid tank 2. In this case, it is necessary to observe the generated droplets from the direction of the second liquid tank 2 located below.

Figure 7:
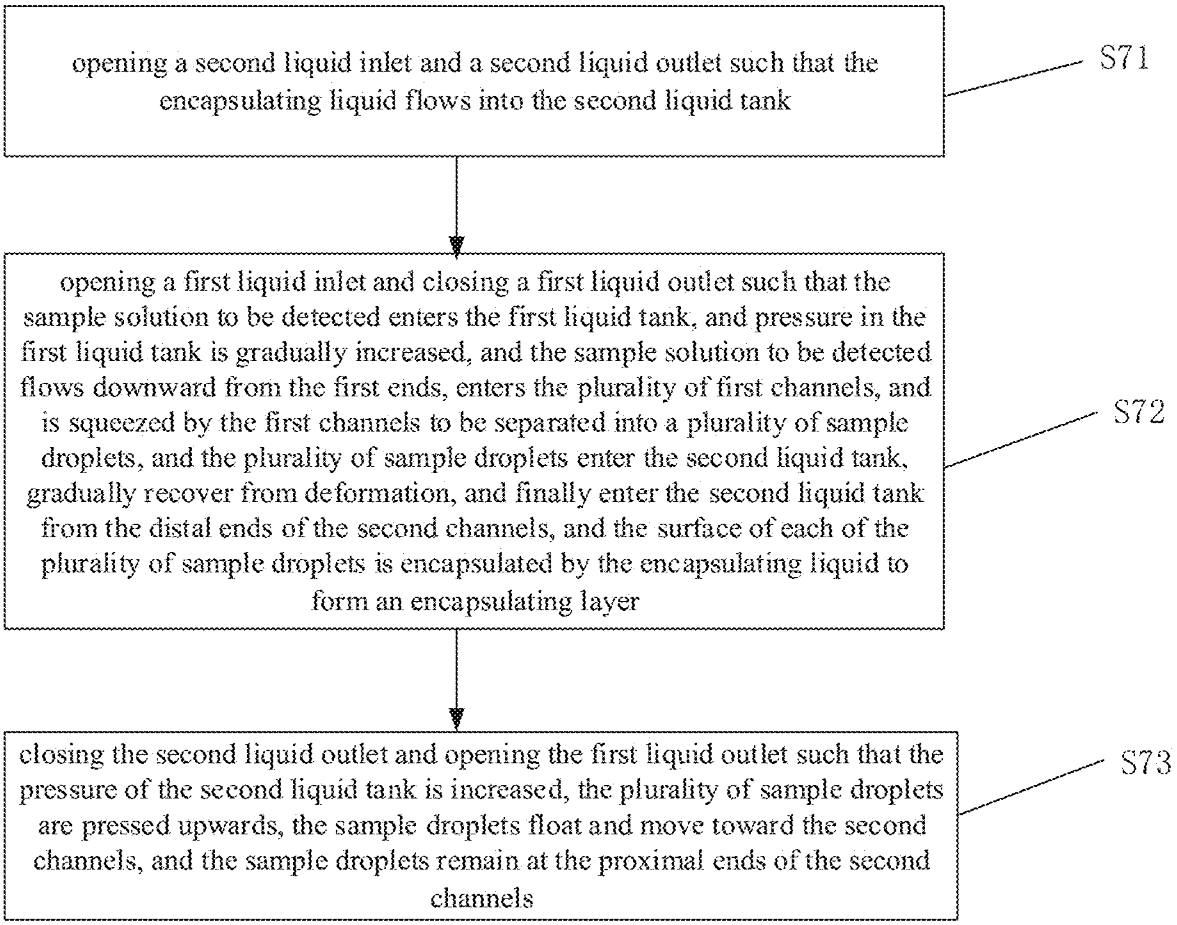
FIG. 7 is a flowchart of a droplet separation method performed by a microfluidic chip according to an embodiment of the present disclosure.

In the embodiment of generating droplets in the inverted mode, as shown in FIG. 7, firstly, in step S71, referring to FIG. 5(*a*2), the first liquid inlet 1*a* is opened, the first liquid outlet 1*b* is closed, the sample solution to be detected enters the first liquid tank 1; the second liquid inlet 2*a* is opened, the second liquid outlet 2*b* is opened, the encapsulating liquid flows into the second liquid tank 2, such that the pressure of the first liquid tank 1 gradually increases, so that under the pressure and the gravity, the sample solution to be detected flows downward from the first ends 311*a* of the first channels 311 of the plurality of microfluidic channels 31, enters the plurality of first channels 311, and is squeezed by the first channels 311 to extract the sample droplets 01.

The increase of the flow rate of the liquid to be detected may accelerate the increase of the pressure of the first liquid tank 1, so that droplets may be generated more quickly. Alternatively, the first liquid outlet 1*b* and the second liquid outlet 2*a* may both be kept open, such that the flow rate of the liquid to be detected is greater than the flow rate of the encapsulating liquid, and the pressure of the first liquid tank 1 is gradually increased.

Further, in step S72, referring to FIGS. 5(*a*2)-(*b*2), the plurality of sample droplets 01 enter the second channels 312 from the second ends 311*b* of the first channels 311, gradually recover from deformation, and finally enter the lower second liquid tank 2 from the distal ends 312*b* of the second channels 312, and flow into the encapsulating liquid in the second liquid tank 2. Since the sample solution to be detected forming the sample droplets 01 is the aqueous phase solution and the encapsulating liquid is the oily solution, the encapsulating liquid will wrap the surface of each sample droplet 01 of the plurality of sample droplets 01 to form the encapsulating layer 02, so as to encapsulate the sample droplet 01 in the encapsulating layer 02, and the stabilizer in the encapsulating liquid will increase the stability of the encapsulating layer 02, and finally, the sample droplets 01 with stable encapsulation environment are formed.

Further, in step S73, referring to FIGS. 5(*b*2)-(*c*2), the second liquid outlet 2*b* is closed, the first liquid outlet 1*b* is opened, such that the pressure of the second liquid tank 2 is increased, the sample droplet 01 are pressed upwards. Since the density of the sample solution to be detected forming the sample droplet 01 is lower than that of the encapsulating liquid, the sample droplets 01 float upwards and move toward the upper second channels 312. Since the diameter d2 of the proximal end 312*a* of the second channel 312 is smaller than the diameter d3 of the sample droplet 01, the sample droplets 01 are finally stopped at the proximal ends 312*a* of the second channels 312. Since the density of the sample solution to be detected is less than that of the encapsulating liquid, the sample droplets 01 may be naturally suspended at the proximal ends 312*a* of the second channels 312, so that the sample droplets 01 may be positioned, and the generation process of the sample droplets 01 is completed. In this embodiment, after the sample droplets 01 are generated and positioned, the sample droplets 01 at the proximal ends 312*a* of the respective second channels 312 may be observed from below the microfluidic chip, i.e., from the outside of a side of the second liquid tank 2 distal to the channel layer 3, so that the sample droplets 01 are not transferred.

It should be noted that in order to observe the sample droplets 01 at the proximal ends 312*a* of the respective second channels 312 from the outside of the side of the second liquid tank 2 distal to the channel layer 3, a bottom surface of the housing which forms the second liquid tank 2 and is distal to the channel layer 3 may be made of a transparent material, such as glass, plastic, etc., which is not limited here.

In some examples, an inner wall of the microfluidic channel 31 may be provided with a thin lyophobic layer 100, as schematically shown in FIG. 2. The lyophobic layer 100 may be made of a material having characteristics of a hydrophobic phase solution, so that when the sample solution to be detected, which is an aqueous phase, flows through the microfluidic channel 31, the sample solution to be detected may be prevented from adhering to the inner wall, waste of the sample solution to be detected is reduced, and the microfluidic channel 31 is prevented from being blocked. In some examples, the material of the lyophobic layer 100 includes a lyophobic group and a reactive group coupled, the lyophobic group is capable of providing characteristics of the hydrophobic phase solution of the lyophobic layer, and the reactive group is capable of reacting with the inner wall of the microfluidic channel 31 to couple the lyophobic group to the inner wall of the microfluidic channel 31 to form the lyophobic layer. The lyophobic group may include various types of chemical substances, for example, an alkane which has a long chain, specifically, an alkane having a carbon number of not less than 6. The reactive group may also include various types of chemicals, and may include at least one of silane, siloxane, oxysilane. The inner wall of the microfluidic channel 31 (i.e. the material of the channel layer 3) has hydroxyl groups, which may react with chemical substances including silane, siloxane, oxysilane, etc., so as to dissociate silicon atoms therein, and combine the hydroxyl groups with the reactive groups having dissociated silicon atoms, thereby coupling lyophobic groups coupled with the reactive groups. If the inner wall of the microfluidic channel 31 does not have hydroxyl groups, a Plasma process may be used to generate hydroxyl groups on the inner wall of the microfluidic channel 31. In this embodiment, the lyophobic layer 100 may also be other chemical substances, which is not limited herein.

In some examples, the channel layer 3 may be made of various types of materials. For example, the channel layer may include at least one of silicon, glass, Polymethyl Methacrylate (PMMA), Polycarbonate (PC), and other polymer materials, which is not limited herein. Depending on the material, the microfluidic channels 31 may be formed in the channel layer 3 by using any one of Micro-Electro-Mechanical systems (MEMS) process compatibility, Micro-injection molding, laser processing, and machining.

In some examples, in the microfluidic chip provided by the embodiment of the present disclosure, the encapsulating liquid forming the encapsulating layer 02 may include the oily solution and the stabilizer. The stabilizer may have various types. For example, the stabilizer may be a polymer having multiple blocks, such as, two blocks, or three blocks. A chemical substance of at least one of the multiple blocks has hydrophobicity, a chemical substance of at least one other block has hydrophilicity, and a volume proportion of the block having hydrophilicity in the polymer is smaller than that of the block having hydrophobicity. The multiple blocks may form a molecular structure of a cone-truncated cone-cylinder type in a spatial dimension to form the polymer. The hydrophilic block will be attached to the sample droplet 01 and the hydrophobic block will not be attached to the sample droplet 01, so that the blocks in the stabilizer spontaneously assemble together to form a stable encapsulating layer 02. Taking the polymer including two blocks as an example, the hydrophilic block in the two blocks may be Polyethylene glycol (PEG), the molecular formula is HO(CH2CH2O)nH; the hydrophobic block may be Polystyrene (PS), the molecular formula is (C8H8)n. Alternatively, the polymer forming the stabilizer may also be other chemical substances, such as propylene oxide and ethylene oxide copolymer, polyoxyethylene sorbitan fatty acid ester, sorbitan tristearate and other high molecular surfactants etc., which is not limited herein.

It should be understood that the above embodiments are merely exemplary embodiments adopted to explain the principles of the present disclosure, and the present disclosure is not limited thereto. It will be apparent to one of ordinary skill in the art that various changes and modifications may be made therein without departing from the spirit and scope of the present disclosure, and these changes and modifications also fall within the scope of the present disclosure.

What is claimed is:

1. A microfluidic chip, comprising: a first liquid tank and a second liquid tank opposite to each other and a channel layer between the first liquid tank and the second liquid tank;

the channel layer comprises a plurality of microfluidic channels which are separated from each other, first ends of the microfluidic channels are communicated with the first liquid tank, and second ends of the microfluidic channels are communicated with the second liquid tank; the first liquid tank is configured to contain sample solution to be detected, and the second liquid tank is configured to contain encapsulating liquid;

the plurality of microfluidic channels are configured to separate the sample solution to be detected entering the first liquid tank into a plurality of sample droplets, and make the plurality of sample droplets enter the second liquid tank such that each of the plurality of sample droplets is encapsulated by the encapsulating liquid.

2. The microfluidic chip according to claim 1, wherein each of the plurality of microfluidic channels comprises a first channel and a second channel which are connected to each other, the first channel is closer to the first liquid tank than the second channel; the second channel has a proximal end proximal to the first channel, and a distal end distal to the first channel; wherein, an aperture of the distal end is larger than that of the proximal end, and an aperture of the second channel is gradually increased along a direction from the first channel to the second channel, and the aperture of the distal end of the second channel is larger than a diameter of the sample droplet.

3. The microfluidic chip according to claim 2, wherein an aperture of the first channel is constant in the direction from the first channel to the second channel, and the aperture of the first channel is smaller than the diameter of the sample droplet.

4. The microfluidic chip according to claim 2, wherein an orthographic projection of the first channel on a plane where the first liquid tank is located is within an orthographic projection of the second channel on the plane where the first liquid tank is located.

5. The microfluidic chip according to claim 2, wherein an orthographic projection of the first channel on a plane where the first liquid tank is located is circular, and an orthographic projection of the second channel on the plane where the first liquid tank is located is circular.

6. The microfluidic chip according to claim 1, wherein the plurality of microfluidic channels extend in a first direction; a plane where the first liquid tank is located is parallel to a plane where the second liquid tank is located; and the first direction is perpendicular to an extending direction of the plane where the first liquid tank is located.

7. The microfluidic chip according to claim 1, wherein the first liquid tank has a first fluid inlet and a first fluid outlet; the second liquid tank has a second liquid inlet and a second liquid outlet; wherein, an included angle between an extending direction of a first connection line between the first liquid inlet and the first liquid outlet and an extending direction of a second connection line between the second liquid inlet and the second liquid outlet is smaller than 90 degrees.

8. The microfluidic chip according to claim 7, wherein the extending direction of the first connection line is parallel to the extending direction of the second connection line.

9. The microfluidic chip according to claim 1, wherein the first liquid tank has a first fluid inlet and a first fluid outlet; the second liquid tank has a second liquid inlet and a second liquid outlet;

the microfluidic chip further comprises: a first driving device and a second driving device; the first driving device is at the first liquid inlet and is configured to drive the sample solution to be detected to flow; the second driving device is at the second liquid inlet and is configured to drive the encapsulating liquid to flow.

10. The microfluidic chip according to claim 9, wherein the first driving device is any one of a pneumatic pump, a plunger pump, and a peristaltic pump; and/or the second driving device is any one of a pneumatic pump, a plunger pump, and a peristaltic pump.

11. The microfluidic chip according to claim 1, further comprising a lyophobic layer on an inner wall of each of the plurality of microfluidic channels and configured to prevent the sample solution to be detected from adhering to the inner wall.

12. The microfluidic chip according to claim 11, wherein a material of the lyophobic layer comprises a lyophobic group and a reactive group which are connected to each other; the lyophobic group comprises an alkane having a carbon number of not less than 6; the reactive group comprises at least one of silane, siloxane, oxysilane.

13. The microfluidic chip according to claim 1, wherein a material of the channel layer comprises at least one of silicon, glass, polymethyl methacrylate, and polycarbonate.

14. The microfluidic chip according to claim 1, wherein a bottom surface of the second liquid tank at a side distal to the channel layer is made of a transparent material.

15. A droplet separation method by using a microfluidic chip, wherein the microfluidic chip comprises: a first liquid tank and a second liquid tank opposite to each other and a channel layer between the first liquid tank and the second liquid tank; the channel layer comprises a plurality of microfluidic channels which are separated from each other, first ends of the microfluidic channels are communicated with the first liquid tank, and second ends of the microfluidic channels are communicated with the second liquid tank; the first liquid tank is configured to contain sample solution to be detected, and the second liquid tank is configured to contain encapsulating liquid;

the droplet separation method comprises enabling the sample solution to be detected entering the first liquid tank to be separated into a plurality of sample droplets through the plurality of microfluidic channels; causing the plurality of sample droplets to enter the second liquid tank; and causing a surface of each of the plurality of sample droplets to be encapsulated by the encapsulating liquid.

16. The droplet separation method according to claim 15, wherein a density of the sample solution to be detected is greater than that of the encapsulating liquid, and each of the plurality of microfluidic channels comprises a first channel and a second channel which are connected to each other, the first channel is closer to the first liquid tank than the second channel; the second channel has a proximal end proximal to the first channel, and a distal end distal to the first channel, and the droplet separation method comprises steps of:

causing the first liquid tank to be below the second liquid tank;

opening a second liquid inlet and a second liquid outlet of the second liquid tank, such that the encapsulating liquid flows into the second liquid tank; and opening a first liquid inlet of the first liquid tank, closing a first liquid outlet of the first liquid tank, such that the sample solution to be detected enters the first liquid tank, and pressure in the first liquid tank is gradually increased, and under the pressure, the sample solution to be detected flows upward from the first ends of the first channels of the plurality of microfluidic channels, enters the plurality of first channels, and is squeezed by the first channels to be separated into a plurality of sample droplets, and the plurality of sample droplets enter the second liquid tank, gradually recover from deformation, and finally enter the second liquid tank from the distal ends of the second channels, and the surface of each of the plurality of sample droplets is encapsulated by the encapsulating liquid to form an encapsulating layer.

17. The droplet separation method according to claim 16, after forming the encapsulating layer, the droplet separation method further comprises:

closing the second liquid outlet, and opening the first liquid outlet such that the pressure of the second liquid tank is increased, the plurality of sample droplets are pressed downward, the sample droplets sink and move toward the second channels, and the sample droplets remain at the proximal ends of the second channels.

18. The droplet separation method according to claim 15, wherein a density of the sample solution to be detected is lower than that of the encapsulating liquid, and each of the plurality of microfluidic channels comprises a first channel and a second channel which are connected to each other, the first channel is closer to the first liquid tank than the second channel; the second channel has a proximal end proximal to the first channel, and a distal end distal to the first channel, and the droplet separation method comprises steps of:

causing the first liquid tank to be above the second liquid tank;

opening a second liquid inlet and a second liquid outlet of the second liquid tank, such that the encapsulating liquid flows into the second liquid tank; and opening a first liquid inlet of the first liquid tank, and closing a first liquid outlet of the first liquid tank, such that the sample solution to be detected enters the first liquid tank, and pressure in the first liquid tank is gradually increased, and the sample solution to be detected flows downward from the first ends of the plurality of microfluidic channels, enters the plurality of first channels, and is squeezed by the first channels to be separated into a plurality of sample droplets, and the plurality of sample droplets enter the second liquid tank, gradually recover from deformation, and finally enter the second liquid tank from the distal ends of the second channels, and the surface of each of the plurality of sample droplets is encapsulated by the encapsulating liquid to form an encapsulating layer.

19. The droplet separation method according to claim 18, after forming the encapsulating layer, the droplet separation method further comprises:

closing the second liquid outlet, and opening the first liquid outlet such that the pressure of the second liquid tank is increased, the plurality of sample droplets are pressed upwards, the sample droplets float and move toward the second channels, and the sample droplets remain at the proximal ends of the second channels.

* * * * *